US00PP09313P

United States Patent [19]

VandenBerg

[11] Patent Number: Plant 9,313

[45] Date of Patent: Oct. 3, 1995

[54] CHRYSANTHEMUM PLANT NAMED 'MADISON'

[75] Inventor: Cornelis P. VandenBerg, Salinas, Calif.

[73] Assignee: Yoder Brothers, Inc., Barberton, Ohio

[21] Appl. No.: 280,525

[22] Filed: Jul. 26, 1994

[51] Int. Cl.[6] ..... A01H 5/00

[52] U.S. Cl. ..... Plt./74.1

[58] Field of Search ..... Plt./74.1, 82.5

[56] References Cited

U.S. PATENT DOCUMENTS

P.P. 7,325 9/1990 VandenBerg ..... Plt./82.5

*Primary Examiner*—Howard J. Locker
*Attorney, Agent, or Firm*—Foley & Lardner

[57] ABSTRACT

A Chrysanthemum plant named Madison particularly characterized by its flat capitulum form; daisy capitulum type; purple-violet and white bi-colored ray floret color; diameter across face of capitulum of 64 to 73 mm when fully opened, when grown as a pinched spray pot mum; photoperiodic flowering response to short days of 50 to 58 days; plant height, with 16 to 21 long days after sticking unrooted cuttings, and with 1 to 2 applications of 2500 ppm B-9 SP, ranges from 23 to 28 cm when grown as a pinched pot mum with four cuttings in a 15 cm pot; branching pattern is spreading and prolific, each plant having 4 to 5 laterals after pinch; and recommended as spray pot mum.

3 Drawing Sheets

The present invention comprises a new and distinct cultivar of Chrysanthemum, botanically known as *Dendranthema grandiflora*, and referred to by the cultivar name Madison.

Madison, identified as 5264 (91-499002), was originated from a cross made by Cornelis P. VandenBerg in a controlled breeding program in Salinas, Calif., in 1990.

The female parent of Madison was an unnamed seedling identified as 6670 (86-880003) and described as a disbud pot mum with flat capitulum form; daisy capitulum type; pink and white bi-colored ray floret color; diameter across face of capitulum of 127 to 133 mm when grown as a pinched disbudded pot mum; flowering response to short days in Salinas, Calif. of 50 to 56 days; plant height of 20 to 28 cm when grown with 15 to 16 long days after sticking unrooted cuttings prior to start of short days, and 1 to 2 applications of 2500 ppm B-9 SP; and a branching pattern of 4 to 5 laterals developing after pinch. The female parent was discarded from all programs in March 1990.

The male parent of Madison was an unnamed seedling identified as 6577 (86-869003), and described as a pot spray mum with flat capitulum form; daisy capitulum type; red and yellow bi-colored ray floret color; diameter across face of capitulum of 70 mm when grown as a pinched spray pot mum; flowering response to short days in Salinas, Calif. of 55 to 63 days; plant height of 23 to 33 cm when grown as a pinched pot spray mum with 14 to 16 long days after sticking unrooted cuttings prior to start of short days, and 1 to 2 applications of 2500 ppm B-9 SP; and a branching pattern of 3 to 5 laterals developing after pinch. The male parent was discarded from all programs in March 1991.

Madison was discovered and selected as one flowering plant within the progeny of the stated cross by Cornelis P. VandenBerg in March 1992, in a controlled environment in Salinas, Calif.

The first act of asexual reproduction of Madison was accomplished when vegetative cuttings were taken from the initial selection in May 1992 in a controlled environment in Salinas, Calif., by technicians working under supervision of Cornelis P. VandenBerg.

Horticultural examination of controlled flowerings of successive plantings has shown that the unique combination of characteristics as herein disclosed for Madison are firmly fixed and are retained through successive generations of asexual reproduction.

Madison has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Madison, which, in combination, distinguish this Chrysanthemum as a new and distinct cultivar:

1. Flat capitulum form.
2. Daisy capitulum type.
3. Purple-violet and white bi-colored ray floret color.
4. Diameter across face of capitulum of 64 to 73 mm when fully opened, when grown as a pinched spray pot mum.
5. Photoperiodic flowering response to short days of 50 to 58 days.
6. Plant height, with 16 to 21 long days after sticking unrooted cuttings, and with 1 to 2 applications of 2500 ppm B-9 SP, ranges from 23 to 28 cm when grown as a pinched pot mum with four cuttings in a 15 cm pot.
7. Branching pattern is spreading and prolific, each plant having 4 to 5 laterals after pinch.
8. Recommended as spray pot mum.

The accompanying photographic drawings show typical inflorescence and leaf characteristics of Madison, with the colors being as nearly true as possible with illustrations of this type.

Sheet 1 is a color photograph of Madison grown as a pinched spray pot mum with four cuttings in a 15 cm pot.

Sheet 2 is a black and white photograph of three views of the inflorescence of Madison.

Sheet 3 is a black and white photograph showing the upper and under sides of the leaves of Madison at 3 stages of development (mature, intermediate and immature).

In sheets 2 and 3 a measuring tape in centimeters has been added.

Of the commercial cultivars known to the inventor, the most similar in comparison to Madison is the cultivar identified as Davis, disclosed in U.S. Plant Pat. No. 7,325. Reference is made to attached Chart A, which compares certain characteristics of Madison to the same characteristics of Davis.

Similar traits are capitulum form and type, and recommendation as a pot spray mum. The purple-violet and white bi-colored color of Madison differs from the solid red-purple ray floret color of Davis. Madison also has a similar to slightly larger diameter of capitulum, an earlier flowering response to short days, and a shorter plant height than Davis, requiring more long days to attain a commercially acceptable plant height than Davis. In some trials Madison also developed one less lateral less after pinching when compared with Davis.

In the following description color references are made to The Royal Horticultural Society Colour Chart. The color values were determined on plant material grown as a pinched spray pot mum in Salinas, Calif. on Apr. 29, 1994.

Classification:

*Botanical.*—*Dendranthema grandiflora* cv Madison.

*Commercial.*—Daisy spray pot mum.

INFLORESCENCE

A. Capitulum:

*Form.*—Flat.

*Type.*—Daisy.

*Diameter across face.*—64 to 73 mm when fully opened.

B. Corolla of ray florets:

*Color (general tonality from a distance of three meters).*—Purple-violet and white bi-color.

*Color (upper surface).*—81C, with margins of the ray florets closest to 155D and slightly streaked with 81C.

*Color (under surface).*—155D, tinged with 62D.

*Shape.*—Longitudinally straight, apex pointed; concave in cross-section.

C. Corolla of disc florets:

*Color (mature).*—14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—23 to 28 cm when grown as a pinched pot mum with four cuttings in a 15 cm pot, and with 16 to 21 long days after direct sticking unrooted cuttings prior to start of short days and 1 to 2 applications of 2500 ppm B-9 SP.

*Branching pattern.*—Spreading and prolific, with 4 to 5 laterals after pinch.

B. Foliage:

*Color (upper surface).*—147A.

*Color (under surface).*—147B.

*Shape.*—Deeply lobed and serrated.

CHART A

COMPARISON OF MADISON AND DAVIS

| CULTIVAR | MADISON | DAVIS |
|---|---|---|
| Ray floret color | Purple-violet and white bi-color | Red-purple |
| Capitulum form and type | Flat daisy | Flat daisy |
| Diameter across face of capitulum | 64 to 73 mm | 64 to 70 mm |
| Flowering response | 50 to 58 days | 55 to 60 days |
| Plant height with | | |
| 16 to 21 long days | 23 to 28 cm | |
| 14 to 16 long days | | 20 to 25 cm |
| Branching pattern | 4 to 5 laterals | 4 to 6 laterals |
| Recommended as | Pot spray mum | Pot spray mum |

COMPARISONS MADE OF PLANTS GROWN AS PINCHED SPRAY POT MUMS IN SALINAS, CALIFORNIA

I claim:

1. A new and distinct Chrysanthemum plant named Madison, as described and illustrated.

* * * * *

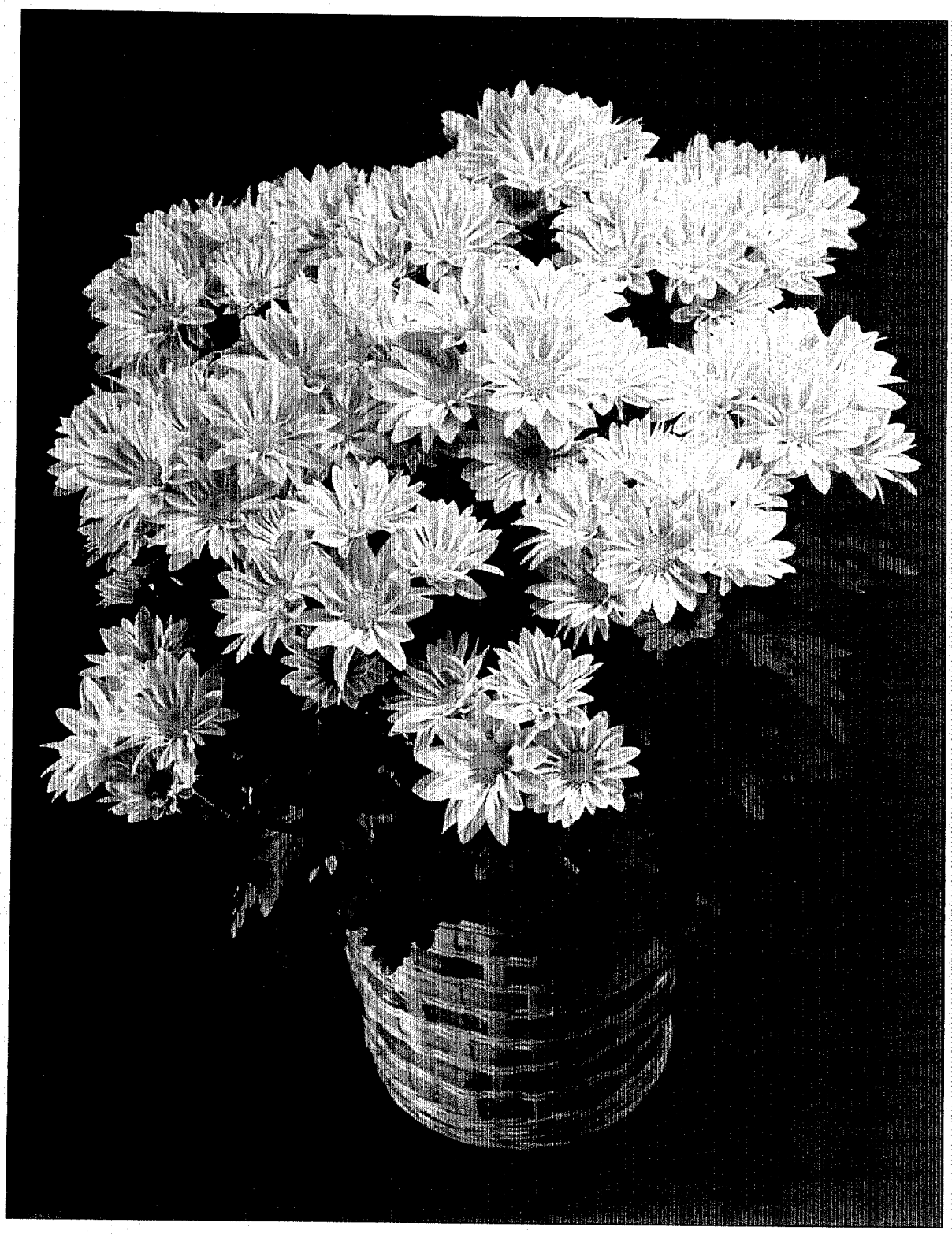

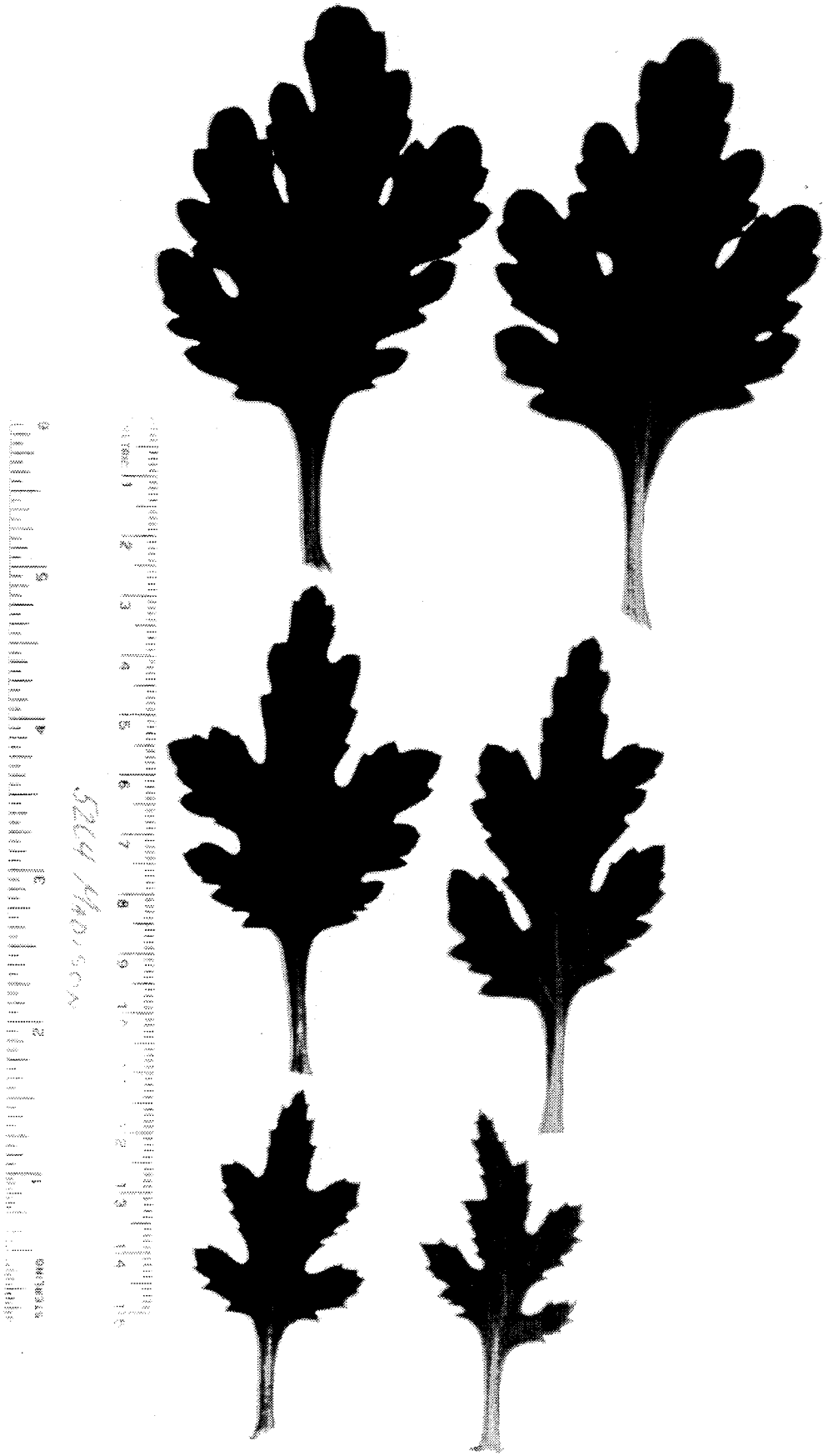

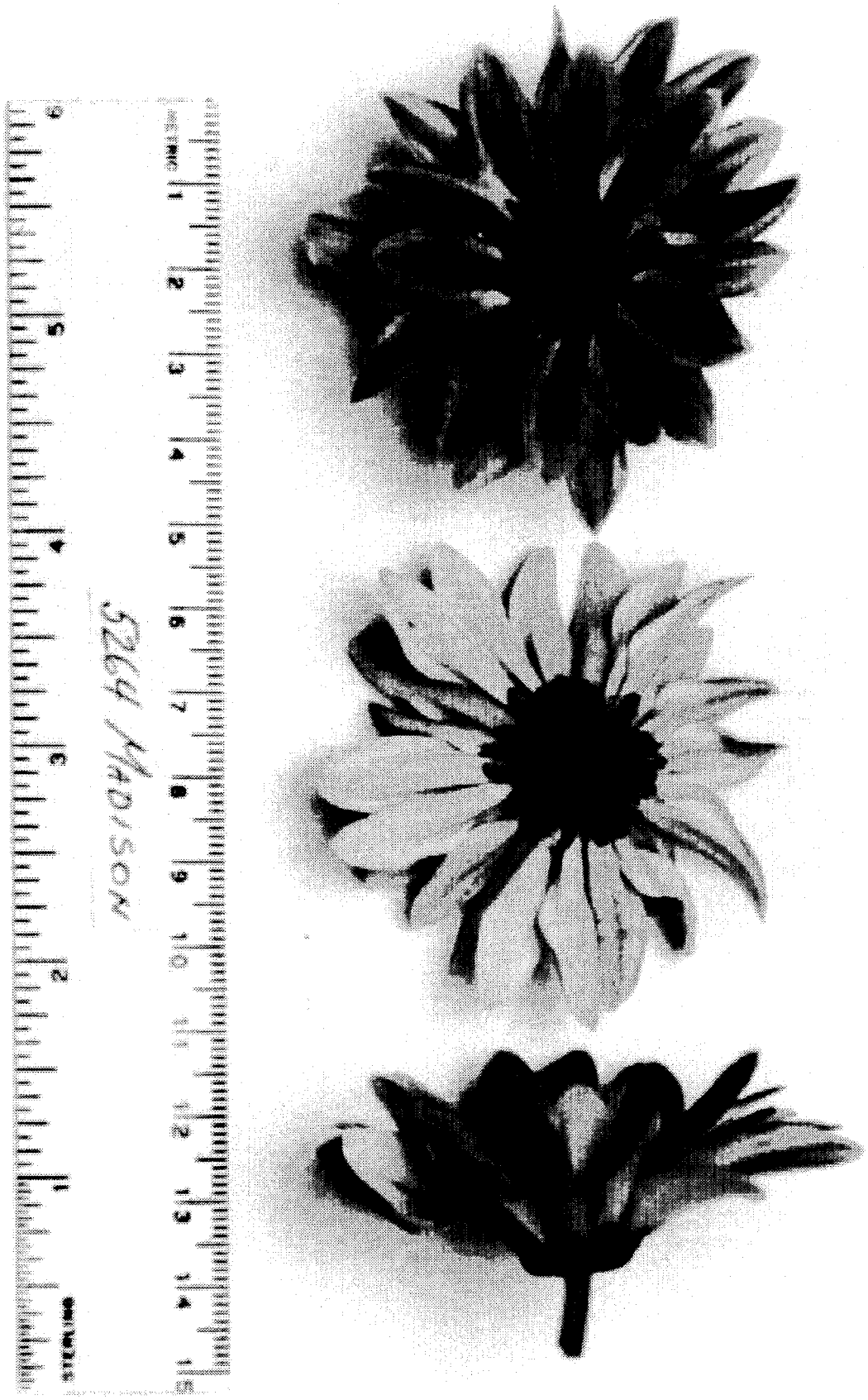
Madison
526H